(12) United States Patent
Lindquist (10) Patent No.: US 6,422,868 B1
(45) Date of Patent: Jul. 23, 2002

(54) IN-OFFICE TOOTH WHITENING

(75) Inventor: Sherrill F. Lindquist, Dublin, OH (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 09/565,752

(22) Filed: May 8, 2000

(51) Int. Cl.[7] .............................................. A61C 5/00
(52) U.S. Cl. ...................................... 433/215; 433/214
(58) Field of Search .............................. 433/213, 214, 433/34, 48, 74, 215, 229

(56) References Cited

U.S. PATENT DOCUMENTS

| | | | |
|---|---|---|---|
| 1,084,017 A | 1/1914 | Lautenburg | |
| 2,110,860 A | 3/1938 | Gremple | |
| 2,257,329 A | 9/1941 | Britt | 128/401 |
| 3,207,161 A | 9/1965 | Dietz | 128/404 |
| 3,215,139 A | 11/1965 | Dietz | 128/172.1 |
| 4,445,854 A | 5/1984 | Bekey et al. | 433/37 |
| 4,959,013 A | 9/1990 | Reynolds | 433/35 |
| 4,983,381 A | 1/1991 | Torres Zaragoza | 424/53 |
| 5,177,120 A * | 1/1993 | Hare et al. | 523/109 |
| 5,211,559 A | 5/1993 | Hart et al. | 433/80 |
| 5,316,473 A | 5/1994 | Hare | 433/29 |
| 5,421,727 A | 6/1995 | Stevens et al. | 433/224 |
| 5,487,662 A * | 1/1996 | Kipke et al. | 433/37 |
| 5,494,441 A | 2/1996 | Nicholson | 433/215 |
| 5,698,610 A * | 12/1997 | Futami et al. | 523/109 |
| 6,102,705 A | 8/2000 | Darnell | 433/216 |

* cited by examiner

*Primary Examiner*—Nicholas D. Lucchesi
(74) *Attorney, Agent, or Firm*—Workman, Nydegger, Seeley (57) ABSTRACT

A dental office procedure for whitening patient teeth involves the basic steps of: (1) heating a specially-prepared patient dentition impression to a temperature in the range of approximately from 110° F. to 130° F.; (2) coating the heated patient dentition impression at impression surfaces corresponding the surfaces of the patient teeth to be whitened with a tooth whitening agent; (3) properly placing the heated and coated patient dentition impression in the patient's mouth; and (4) retaining the so-placed patient dentition impression in position at least for a total period of time in the range of approximately from 5 to 20 minutes. The procedure can be adapted to microwave heating, electrical resistance heating, and hot fluid heating of the patient dentition impression.

17 Claims, 6 Drawing Sheets

IN-OFFICE TOOTH WHITENING

CROSS-REFERENCES

None.

FIELD OF THE INVENTION

This invention relates generally to patient dentition stain removal, and particularly concerns methods, materials, and apparatus which may be advantageously utilized in connection with the whitening or bleaching of patient teeth in a dental office.

BACKGROUND OF THE INVENTION

Present conventional dental practice in the United States for effectively changing the inherent color of patient's teeth basically involves: (1) an in-office teeth whitening procedure that generally requires about one-hour of office time, and (2) in-office preparation of a patient kit with instructions, followed by patient use of the kit in teeth whitening treatments at home of from 1 to 8 hours per day repeated for 2 to 6 weeks.

The in-office teeth whitening procedure usually involves, with a protective rubber dam in place in the patient's mouth: (1) protectively coating the patient's gingival tissues; (2) applying to and activating on the teeth to be whitened an extremely caustic, light-activated, hydrogen peroxide or carbamide peroxide gel, and: (3) afterwards completing a thorough mouth rinse and removal of the protective coating and rubber dam.

The dentist-prepared kit for patient home-use typically includes a custom-configured patient bleaching tray or mouth-guard formed by a multi-step in-office procedure, a supply of whitening agent such as carbamide peroxide gel, and appropriate instructions for kit home-use by the patient. The typical multi-step dental office procedure utilized for forming the custom patient tooth-whitening mouth-guard or tray for home use is a time-consuming procedure, and typically involves the basic steps of: (1) making conventional alginate impressions of the patient's maxillary and/or mandibular teeth, (2) casting dentition models using state-of-the-art dental laboratory stone casting material and the alginate impressions followed by trimming-away of un-needed model material, (3) blocking out on the trimmed cast stone models, using a conventional light-cured or light-activated, acrylic-based resin laboratory block-out gel, those tooth areas to be whitened (often excluding all molar teeth), and (4) vacuum forming a 5-inch by 5-inch sheet of 0.040-inch to 0.080-inch thickness clear plastic resin mouth guard material over each blocked-out and trimmed dental stone model, cooling, removing from model, and suitably trimming above the gingival crest. The whitening mouth guard is then ready for delivery to the patient in the patient home-use whitening kit. As indicated above, home-use of the kit mouth guard and kit-included whitening agent (e.g., carbamide peroxide) typically requires 1 to 8-hour bleaching treatments repeated daily over a period that generally is in the range of 2 to 6 weeks depending upon the degree or severity of dentition staining.

I have discovered a novel in-office dental procedure that, when utilized as a replacement for the above-described conventional in-office procedures, obtains equally satisfactory whitening results, realizes a significant reduction of required dentist and patient in-office times, and also effects a substantial reduction in the costs of patient teeth whitening treatments.

Other objects and advantages of the present invention will become apparent from consideration of the detailed descriptions, drawings, claims, and abstract which follow.

SUMMARY OF THE INVENTION

A preferred embodiment of the method aspect of the present invention involves the sequential steps of: (1) applying a dental impression adhesive to the surface of the principal cavity of a conventional alginate dental impression tray; (2) applying dental wax sheet overlays to the surfaces of the patient's teeth that are to be whitened; (3) filling the coated principal cavity of the dental impression tray with an unset conventional alginate dental impression material; (4) properly placing the filled dental impression tray in the patient's mouth and holding same in place a sufficient length of time to set the unset alginate dental impression material and thereby form a patient dentition impression; (5) removing the alginate dental impression tray and included set alginate patient dentition impression with retained wax overlay material from the patient's mouth; (6) scraping or otherwise removing the retained wax overlay from the alginate patient dentition impression; (7) heating the alginate dental impression tray and included patient alginate dentition impression with radiated microwave energy to a temperature in the range of approximately from 110° F. to 130° F.; (8) coating the surfaces of the patient dentition impression corresponding to the patient teeth that are to be whitened with a conventional carbamide peroxide tooth bleaching gel; (9) promptly and properly placing the heated alginate dental impression tray and included alginate patient dentition impression with carbamide peroxide coating in the patient's mouth, (10) holding the same in place until the alginate patient dentition impression temperature has dropped to below approximately 110° F.; (11) repeating the sequence of steps (7) through (10); and (12) removing the alginate dental impression tray and included alginate patient dentition impression from the patient's mouth and thoroughly rinsing the patient's mouth prior to release of the patient.

In the preferred embodiment of the method aspect of the present invention instances the above step (7) is accomplished using a domestic microwave oven for a very short period of time; and the step (10) which follows will generally require a total holding-in-place time of approximately 6 to 10 minutes to obtain satisfactory tooth whitening results.

The instant invention also involves electrical resistance heating apparatus for dental office use in those instances wherein either the conventional dental impression material is microwave energy "transparent" or wherein microwave oven equipment is not available or desirable. Alternatively, the instant invention involves heated fluid apparatus for dental office use in those instances wherein either the conventional dental impression material is microwave energy "transparent" or wherein microwave oven equipment is not available or desirable.

DETAILED DESCRIPTION

Figure 1:
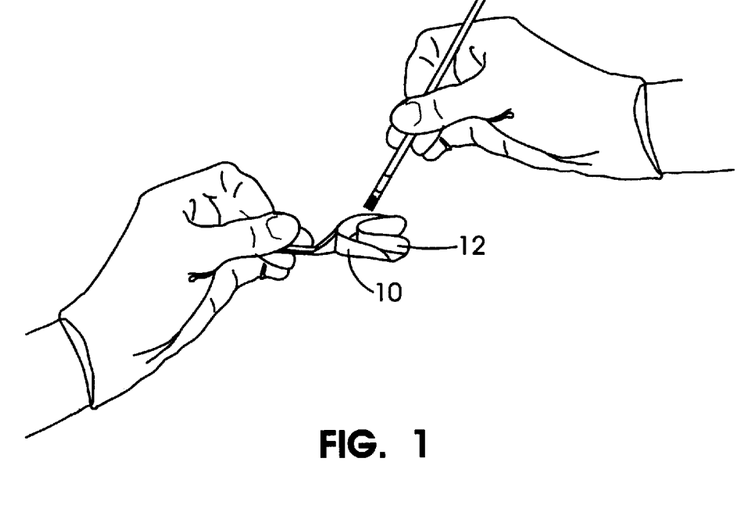
FIG. 1 pictorially depicts a preliminary procedural step of coating the principal cavity of an alginate dental impression tray with a conventional adhesive.

As illustrated in FIG. 1, a somewhat preliminary step to practice of the present invention involves brushing or otherwise applying a dental impression adhesive coating on or to the surface of the principal cavity 12 of a conventional, disposable mandibular alginate dental impression tray 10. One such tray is required for the mandibular teeth that are to be whitened, and a separate but like tray may be used for treating the patient's maxillary teeth. Use of a disposable maxillary "horse-shoe" dental impression tray is not required.

Figure 2:
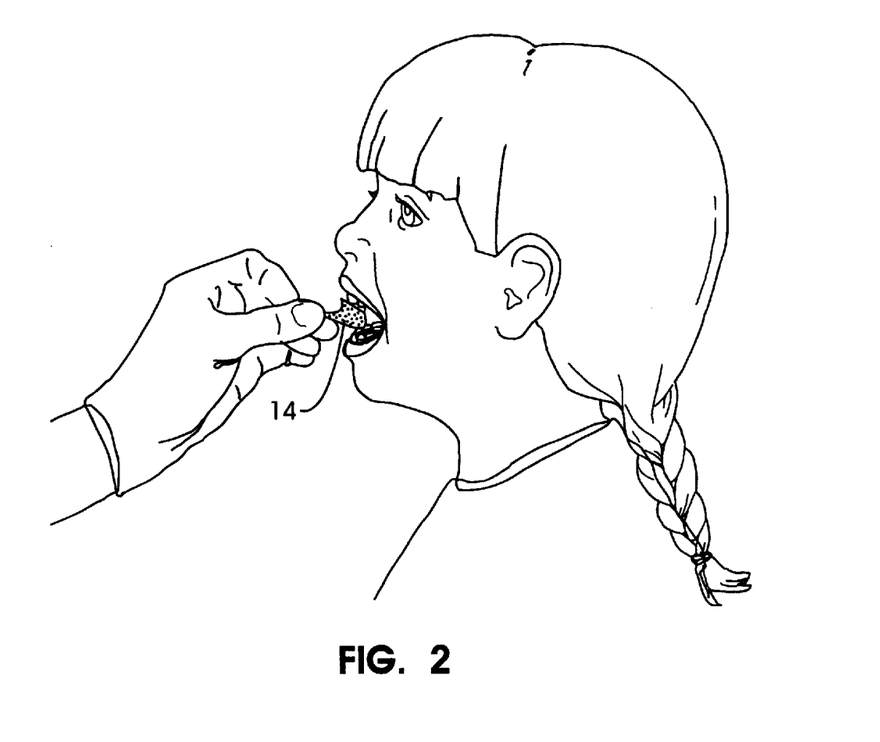
FIG. 2 pictorially depicts another preliminary step of applying a dental wax overlay to the surfaces of the patient's teeth that are to be whitened.

Also, and somewhat as a preparatory step in the practice of this invention, is the procedural step of applying a sheet-like conventional dental wax overlay 14 to those surfaces of the patient's teeth that are to be whitened—usually just to facial aspects of the teeth. See FIG. 2. A thickness of the sheet-like wax material is preferably applied in this step of the invention method.

Figures 3, 4:
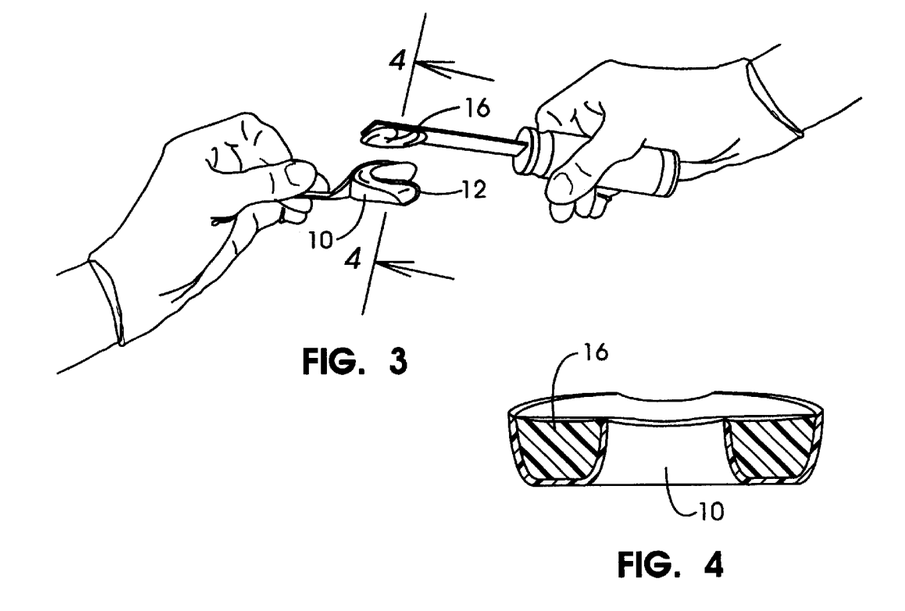
FIG. 3 pictorially illustrates the step of placing an unset conventional dental impression material in the principal cavity of the dental impression tray of FIG. 1.
FIG. 4 is a section view taken at line 4—4 of FIG. 3 and extending transversely through the filled dental impression tray of FIG. 3.
Figure 5:
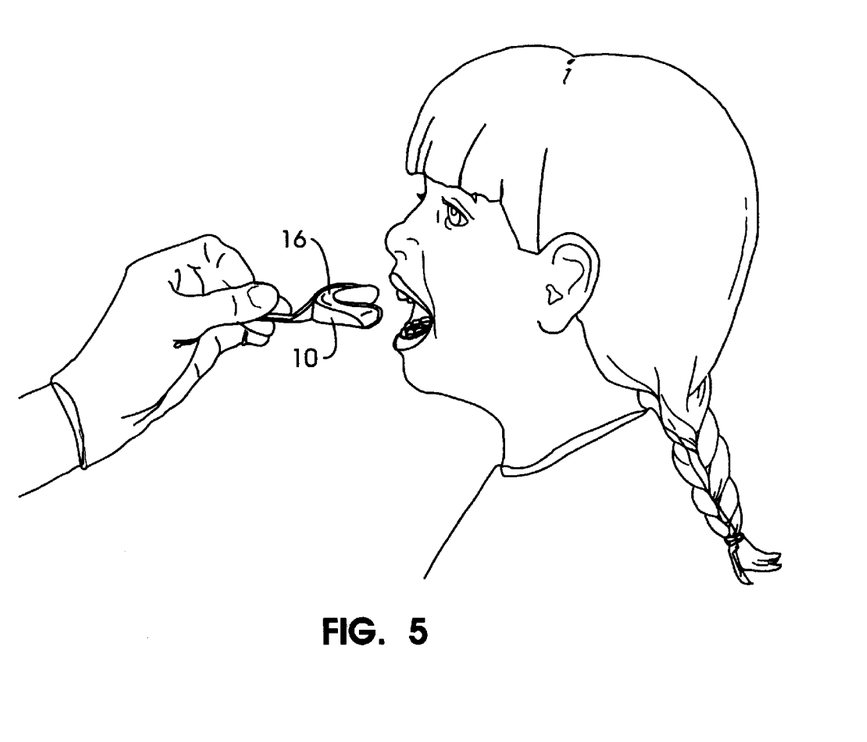
FIG. 5 depicts insertion of the compound-filled dental impression tray of FIGS. 3 and 4 in the patient's mouth for impression-setting purposes.

Referring to FIG. 3, the next step in the invention method involves filling cavity 12 of impression tray 10 with a suitable quantity of a pre-mixed and unset alginate dental impression material or catalyzed dental impression compound 16. FIG. 4 illustrates the filled dental impression tray in its condition just prior to insertion in the patient's mouth. The so-filled dental impression tray is then placed and properly seated in the patient's mouth and held in position for a sufficient length of time for dental impression material 16 to become set. See FIG. 5.

Figures 6, 7:
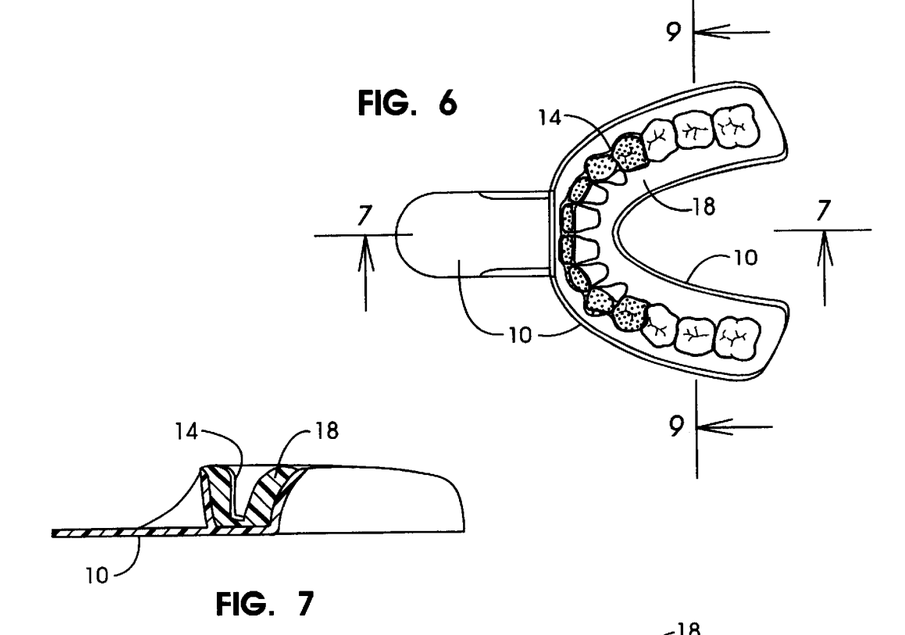
FIG. 6 is a plan view of the completed dental impression prior to wax overlay removal.
FIG. 7 is a section view taken at line 7—7 of FIG. 6.
Figure 8:
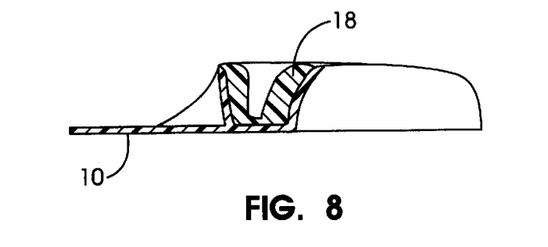
FIG. 8 is a section view similar to FIG. 7 but after accomplishing wax overlay removal.
Figure 9:
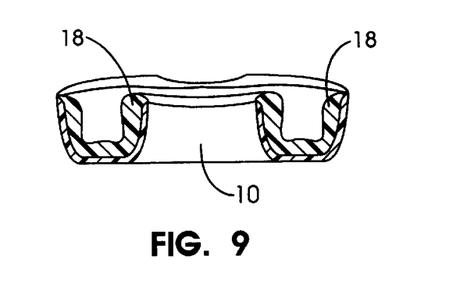
FIG. 9 is a section view taken at line 9—9 of FIG. 6.

Following removal of dental impression tray 10 with its included formed patient dental impression 18 from within the patient's mouth, all wax overlay material 14 that is retained on the surfaces of patient dentition impression 18 is next manually removed from the impression by appropriate manual scraping or the like. FIG. 7 depicts the set patient dentition impression 18 with wax overlay material 14 in place. FIG. 8 is similar to FIG. 7 but illustrates the formed patient dental impression 18 with the wax overlay material removed.

Next, tray 10 and set patient dentition impression 18 are heated to a temperature in the range of approximately from 110° F. to 130° F. I have found that a very satisfactory way of accomplishing this step of the invention method, particularly when the dentition impression is made of a material that absorbs radiated microwave energy as in the case of alginate-base dental impression materials, involves heating the tray and its included patient dental impression in a domestic microwave oven (usually having a 600 watt input electrical energy rating) at oven full power for approximately 10 seconds.

Figure 11:
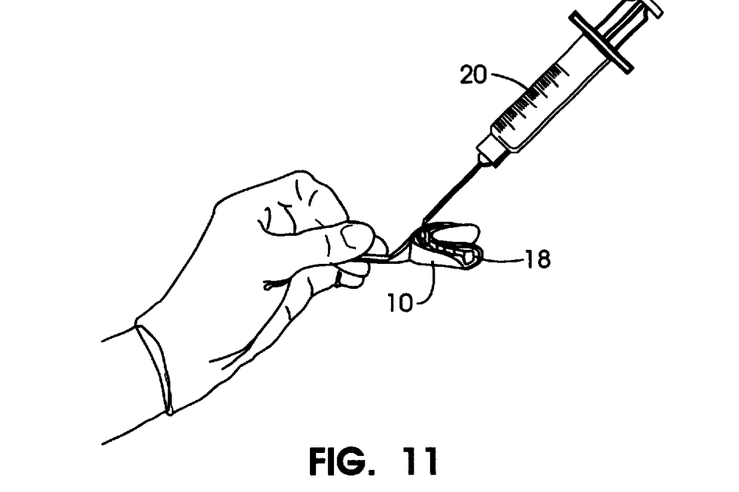
FIG. 11 depicts the application and coating, after prior heating of the dental impression tray and contained set patient dental impression, of a carbamide peroxide gel to the impression surfaces of the patient teeth that are to be whitened.
Figure 12:
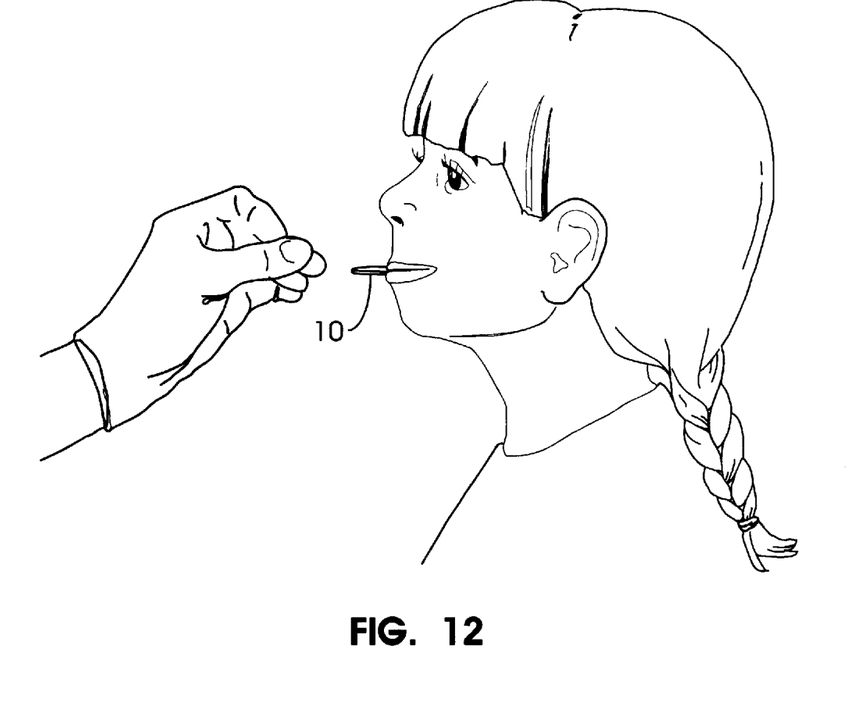
FIG. 12 depicts placement of the whitening tray of FIG. 11 in the patient's mouth.

Quickly, and typically using a syringe 20 (FIG. 11) which preferably contains a 15% carbamide peroxide gel whitener or bleaching agent, with fluoride additive, the surfaces of the set patient dentition impression 18 which correspond to the patient tooth surfaces that are to be bleached are coated in their labial areas with approximately 0.5 to 1 cc. of the syringe whitening gel contents. The so-coated and heated dental impression tray/patient dental impression is then promptly and properly placed in the patient's mouth (see FIG. 12) and held in place until its temperature falls to below approximately 110° F.

Normally the invention method holding periods or period involve(s) a total time-at-temperature of about 3 to 10 minutes to obtain tooth whitening results that are comparable to those obtained by the prior art practice described above. In order to obtain a satisfactory degree of tooth whitening by the hereinbefore described inventive process, and particularly in the case of non-electrical resistance heating applications, it may be necessary to repeat both the patient dental impression heating step and the carbamide peroxide gel-coating and impression placement and holding steps illustrated with FIGS. 11 and 12 in order to obtain the preferred total time-at-temperature. Thus, and with the described process step repeat, the total in-office teeth bleaching or whitening time will generally be in the range of from about 10 minutes to about 20 minutes.

It should be noted that the space filled by the whitening gel following proper tray and patient dental impression insertion into the patient's mouth essentially corresponds to the space or volume occupied by the initially-applied and later-removed dental blocking wax overlay 14.

Figure 10:
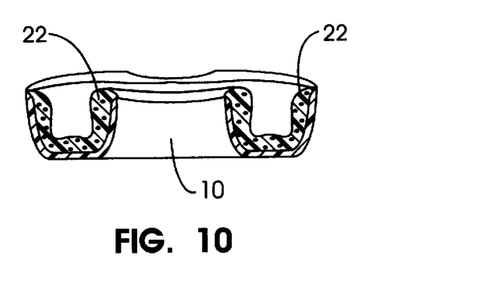
FIG. 10 is a section view taken at line 9—9 of FIG. 8 but with an included different and often-preferred dental impression material.

As shown in FIG. 10, a modified dental impression material 22 may also be utilized in the practice of the present invention. Unset conventional dental impression material utilized to fill the principal cavity 12 of dental impression tray 10 may be advantageously modified to include, as an additive, a fine, particulate material having a specific heat that is greater than the specific heat of the unmodified dental impression material. As an example, I may add and uniformly mix polished, 2 mm.–3 mm. size, stone chips into unset alginate dental impression composition in the ratio of approximately 12½ parts by weight of polished dental stone chips to approximately 87½ parts by weight of unset alginate dental impression material. Inclusion of the aggregate in the composition extends the length of time for which the patient dental impression, following heating by microwave oven equipment, will remain above the minimum temperature of the preferred 110° F. to 130° F. process temperature range while being held in the patient's mouth.

Figure 13:
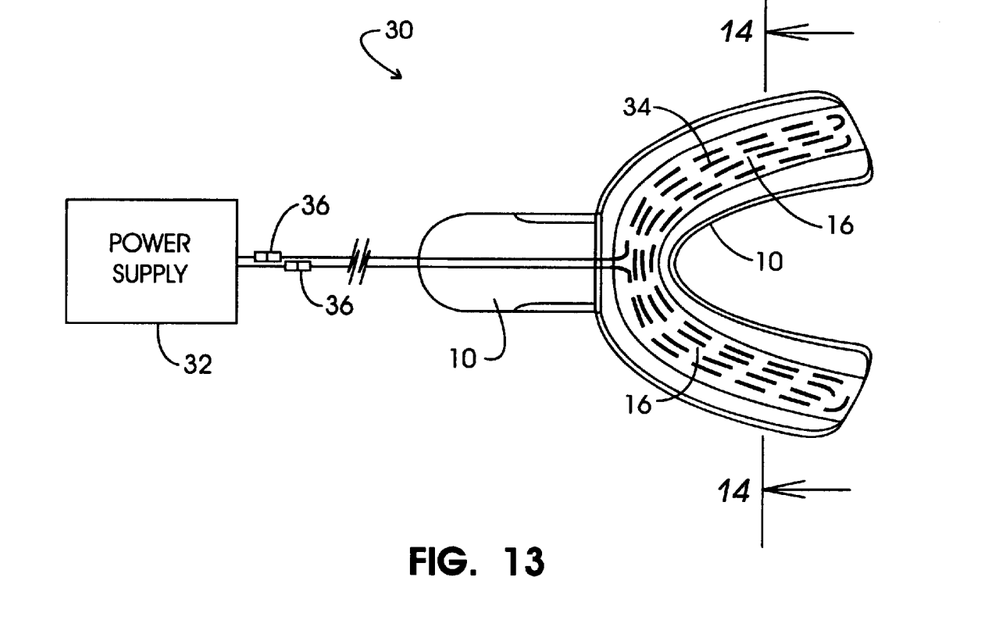
FIG. 13 schematically depicts apparatus utilized for an alternate method of heating and maintaining the proper temperature of the set dental impression material.
Figure 14:
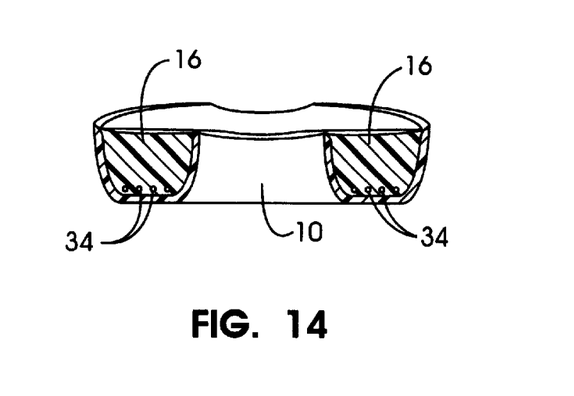
FIG. 14 is a section view taken at line 14—14 of FIG. 13.

FIGS. 13 and 14 pertain to an alternate approach to accomplishing the in-office dental procedure of the present invention for whitening patient teeth utilizing apparatus 30. Such apparatus is basically comprised of a power supply 32 and a looped electrical resistance heating element 34 connected to power supply using conventional electrical disconnects 36. Instead of heating a dental impression tray 10 and its included patient dental impression 18 or 20 in microwave oven equipment, the dental impression tray 10 is provided with looped heating element 34 in the bottom of principal cavity 12 prior to filling the cavity with unset or uncured dental impression material 16. In one application of apparatus 30, I utilized approximately from 40 to 50 inches of No. 24 insulated audio speaker wire as resistance heating element 34. Power supply 32 was basically comprised of a conventional 120/30 volt alternating current step-down transformer with a 2.5 ampere output current, an alternating current-to-direct current rectifier, an electronic intermittent switch having 30–40 second on times alternated with 30–40 second off times, and system on-off timer switch mechanism. The power supply timer functioned to activate power supply 32 for periods of time in the range of from 1 to 15 minutes.

Figure 15:
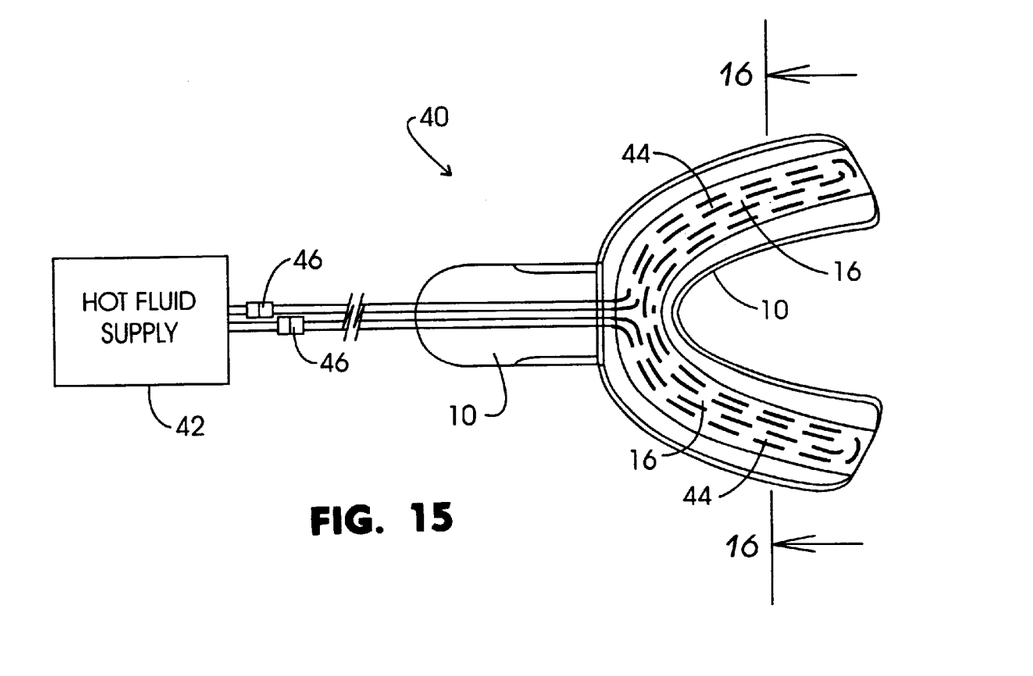
FIG. 15 schematically depicts apparatus for another alternate method of heating and maintaining the proper temperature of the set dental impression material.
Figure 16:
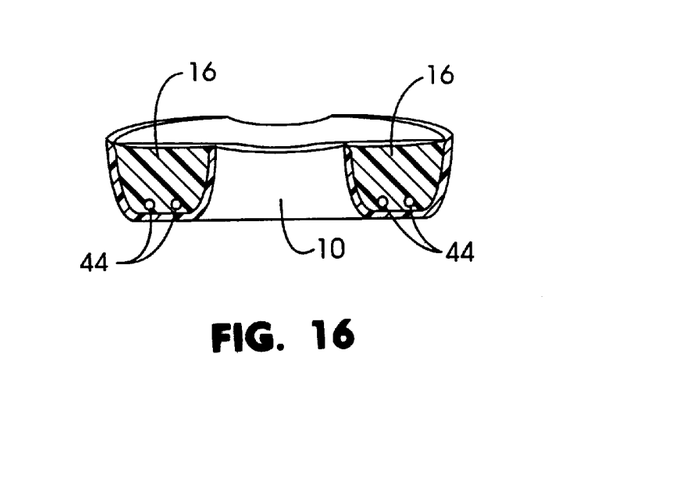
FIG. 16 is a section view taken at line 16-6 of FIG. 15.

FIGS. 15 and 16 pertain to a second alternate approach to accomplish the in-office dental procedure of the present invention for whitening patient teeth utilizing apparatus 40. Such apparatus is basically comprised of a hot fluid supply 42 and a looped tubular fluid conduit 44 connected to hot fluid supply 42 utilizing conventional fluid connectors 46. In this embodiment, the dental impression tray 10 is provided with looped fluid conduit 44 in the bottom of principal cavity 12 prior to filling the cavity with unset or uncured dental impression material 16. In one application of apparatus 40, I utilized a $1/8^{th}$ inch rigid plastic fluid conduit as fluid conduit 44 connected to a supply 42 of water heated to approximately 130° F. Satisfactory results were obtained where the apparatus was retained in a patient's mouth for a least total period of time in the range of approximately from 5 minutes to 20 minutes.

Utilizing such electrical resistance heating equipment or such fluid heating equipment generally avoids the necessity of utilizing the repeated step sequence of dental impression tray and included patient dentition impression reheating in a microwave oven, re-coating portions of the patient dental impression with carbamide peroxide or other teeth bleaching agent, and reinserting and retaining the heated and coated patient dental impression in the patient's mouth for an additional period of time in order to obtain the desired teeth of tooth whitening. Also, the use of such electrical resistance heating apparatus or such fluid heating equipment is a necessity in those cases wherein the dental impression material is microwave energy "transparent" as in the case of catalyzed epoxy-based dental impression compounds.

Various changes may be made to the method steps, materials, and apparatus described above without departing from the scope, meaning, or intent of the claims which follow.

I claim as my invention:

1. Apparatus for in-office dental use to whiten a patient's teeth, and comprising:

a dental impression tray having a principal cavity;

an electrical resistance heating element positioned in said dental impression tray principal cavity;

a formed patient dentition impression positioned in said dental impression tray and embedding said electrical resistance heating element; and an electrical power supply removably connected to said electrical resistance heating element, said electrical power supply controllably energizing said electrical resistance element and heating said formed patient dentition impression to a maintained temperature in the range of approximately from 110° F. to 130° F. for a total period of time in the range of approximately from 5 minutes to 15 minutes.

2. A mixed material for making a patient dentition impression used in a dental office procedure for whitening patient tooth surfaces, and comprising a mixture of a curable dental impression material having a known specific heat and of fine, particulate aggregate having a specific heat substantially greater than said dental impression material known specific heat.

3. The mixed material invention defined by claim 2, and wherein said curable dental impression material is an alginate dental impression material, and said fine, particulate aggregate is fine particulate stone chips.

4. The mixed material invention defined by claim 3, and wherein said alginate curable dental impression material and said fine particulate stone chips are mixed in a ratio of approximately 80 to 90 parts by weight dental impression material and the balance fine particulate stone chips.

5. In a dental office procedure for whitening tooth surfaces of a patient's dentition, a method comprised of using an impression material to form a dentition impression, placing a tooth whitening agent within the dentition impression, placing the dentition impression with the tooth whitening agent contained therein in contact with patient tooth surfaces that are to be whitened, and heating the dentition impression in order to maintain the tooth whitening agent at a temperature in the range of approximately from 110° F. to 130° F. for a total period of time in the range of approximately from 5 minutes to 20 minutes.

6. The dental office procedure invention defined by claim 5, wherein said total period of time is in range of approximately from 5 minutes to 10 minutes.

7. The dental office procedure invention defined by claim 6, and wherein said tooth whitening agent is carbamide peroxide bleaching agent gel.

8. The dental office procedure invention defined by claim 5, and wherein said tooth whitening agent is carbamide peroxide bleaching agent gel.

9. In a dental office procedure for whitening particular tooth surfaces of a patient's dentition, a method comprised of:

using an impression material to make a patient dentition impression with included surface areas that register with the patient tooth surfaces that are to be whitened;

applying a tooth whitening agent to said patient dentition impression included surface areas;

heating said patient dentition impression and the applied tooth-whitening agent and said patient dentition impression to temperatures in the range of approximately from 110° F. to 130° F.;

inserting said heated patient dentition impression with applied and heated tooth whitening agent into the patient's mouth with said patient dentition impression included surface areas in registration with the particular patient tooth surfaces that are to be whitened; and maintaining said inserted heated patient dentition impression at temperatures within said temperature range for a total period of time at least in the range of approximately from 5 minutes to 20 minutes.

10. The dental office procedure invention defined by claim 9, and wherein said total period of time is in a range of approximately from 5 minutes to 10 minutes.

11. The dental office procedure invention defined by claim 10, wherein said tooth whitening agent is carbamide peroxide bleaching agent gel, and wherein said patient dentition impression is an alginate patient dentition impression.

12. The dental office procedure invention defined by claim 9, and wherein said tooth whitening agent is carbamide peroxide bleaching agent gel.

13. In a dental office procedure for whitening particular tooth surfaces of a patient's dentition, a method comprising:

provjding a blocking overlay upon the particular patient tooth surfaces that are to be whitened;

providing a dental impression tray having a principal cavity with a principal cavity adhesive coating;

placing unset dental impression material in said dental impression tray adhered to said dental impression tray principal cavity adhesive coating;

setting said unset dental impression material in the patient's mouth and with said unset dental impression material in contact with the patient's dentition to thereby form a patient dentition impression with included particular patient tooth surface overlay impressions;

applying a tooth whitening agent coating upon said patient dentition impression included particular patient tooth surface overlay impressions;

heating said patient dentition impression and included coated particular patient tooth surface overlay impressions to a temperature in the range of approximately from 110° F. to 130° F.;

placing said heated patient dentition impression and included coated particular patient tooth surface overlay impressions in the patient's mouth in proper registration with the patient dentition tooth surfaces to be whitened; and maintaining said heated patient dentition impression and included coated particular patient tooth surface overlay impressions at a temperature in said temperature range for a total period of time in the approximate range of from 5 minutes to 20 minutes.

14. The dental office procedure invention defined by claim 13, wherein said total period of time is in a range of approximately from 5 minutes to 10 minutes.

15. The dental office procedure invention defined by claim 13, wherein said tooth whitening agent is carbamide peroxide bleaching agent gel, and wherein said patient dentition impression is an alginate patient dentition impression.

16. The dental office procedure invention defined by claim 14, and wherein said tooth whitening agent is carbamide peroxide bleaching agent gel.

17. Apparatus for in-office dental use to whiten a patient's teeth, and comprising:

a dental impression tray having a principal cavity;

a fluid conduit element positioned in said dental impression tray principal cavity;

a formed patient dentition impression positioned in said dental impression tray and embedding said fluid conduit element; and a heated fluid supply removably connected to said fluid conduit element, said heated fluid supply providing heated fluid to said fluid conduit and heating said formed patient dentition impression to a maintained temperature in the range of approximately from 110° F. to 130° F. for a total period of time in the range of approximately from 5 minutes to 20 minutes.

* * * * *